United States Patent

Bielefeldt et al.

Patent Number: 5,536,890
Date of Patent: Jul. 16, 1996

[54] PROCESS FOR PREPARING HEXAFLUOROBUTANE

[75] Inventors: Dietmar Bielefeldt, Ratingen; Albrecht Marhold, Leverkusen, both of Germany

[73] Assignee: Bayer Aktiengesellschaft, Leverkusen, Germany

[21] Appl. No.: 335,739

[22] PCT Filed: May 3, 1993

[86] PCT No.: PCT/EP93/01073

§ 371 Date: Nov. 4, 1994

§ 102(e) Date: Nov. 4, 1994

[87] PCT Pub. No.: WO93/23354

PCT Pub. Date: Nov. 25, 1993

[30] Foreign Application Priority Data

May 14, 1992 [DE] Germany .......................... 42 15 876.1

[51] Int. Cl.⁶ .................. C07C 17/26; C07C 17/354; C07C 19/09
[52] U.S. Cl. ............... 570/175; 570/153; 570/171
[58] Field of Search ....................... 570/171, 155, 570/175

[56] References Cited

U.S. PATENT DOCUMENTS

| 4,902,839 | 2/1990 | Bielefeldt et al. ....................... 570/175 |
| 5,382,720 | 1/1995 | Ikawa et al. ............................ 570/171 |

FOREIGN PATENT DOCUMENTS

| 2036221 | 8/1991 | Canada . |
| 499984 | 8/1992 | European Pat. Off. . |

OTHER PUBLICATIONS

Chemistry Letters (1990)—Mar. 5, pp. 879–880.
Chemistry Letters (1991)—Jul. 9, pp. 1825–1826.

Primary Examiner—Joseph E. Evans
Attorney, Agent, or Firm—Joseph C. Gil

[57] ABSTRACT

1,1,1,4,4,4-hexafluorobutane is obtained from a trifluoroethane compound, by reacting this with hydrogen in the gas phase and without a diluent on a palladium- and/or nickel-containing supported catalyst and subsequently hydrogenating the reaction product.

6 Claims, No Drawings

PROCESS FOR PREPARING HEXAFLUOROBUTANE

This application is a 371 of PCT/EP93/01073 May 03, 1993.

The present invention relates to an improved process for preparing 1,1,1,4,4,4-hexafluorobutane, i,e, a saturated, fluorine-containing and chlorine-free hydrocarbon such as has recently been of interest as a blowing gas for polyurethane foams (as a substitute for CFCs). It is known, from Chem. Lett. 1990, 870–880, that in the case of the compound $CCl_2F$—$CClF_2$ in the presence of hydrogen on a nickel catalyst, an intramolecular elimination of hydrogen chloride takes place with the formation of the unsaturated, chlorine-containing compound $CClF$=$CF_2$. Dimerisation to give butane or butene derivatives does not occur.

It is known, from Chem. Lett. 1991, 1825–1826, that chlorine-containing butenes are formed from the compound $CF_3$—$CCl_3$ in the presence of hydrogen, with argon as a diluent, on a nickel catalyst, due to dimerisation. Under these conditions, $CF_3$—$_{CHC}1F$ and small proportions of a perhalogenated butane derivative are formed from the compound $CF_3$—$CFCl_2$.

A process for preparing 1,1,1,4,4,4-hexafluorobutane has now been found which is characterised in that a trifluoroethane compound of the formula (I)

$$CF_3\text{—}CXYZ \qquad (I),$$

in which

X and Y independently of each other represent hydrogen, chlorine or bromine and z represents chlorine or bromine, is reacted with hydrogen in the gas phase and without a diluent, on a palladium- and/or nickel-containing supported catalyst, and the reaction product, optionally after separation of 1,1,1,4,4,4-hexafluorobutane, is subsequently hydrogenated.

The trifluoroethane compounds of the formula (I) required as starting compounds for the process according to the invention are easily accessible and commercially available products.

$CF_3$—$CCl_3$, $CF_3$—$CHCl_2$ or $CF_3$—$CH_2Br$ are preferably used in the process according to the invention.

Reaction of the trifluoroethane compounds of the formula (I) with hydrogen may take place, for example, in such a way that the compound of the formula (I) is evaporated and passed in gaseous form together with hydrogen over the palladium- and/or nickel-containing supported catalyst. 5 to 200 Nl of hydrogen can be used, for example, for every 100 g of compound of the formula (I). This amount is preferably 10 to 30 Nl of hydrogen.

Reaction of compounds of the formula (I) with hydrogen is performed in the absence of diluents (e.g. argon or nitrogen).

Suitable catalysts for this reaction are, for instance, those which contain 0.5 to 20 g of palladium and/or 100 to 1000 g of nickel per litre. The catalysts preferably contain 1 to 10 g of palladium and/or 300 to 800 g of nickel per litre. The palladium and/or nickel is preferably present completely, or at least partly, in elemental form. Suitable support materials for these catalysts are, for instance, silicon dioxide, silicates, aluminium dioxide, spinels, barium sulphate, titanium dioxide, magnesium oxide and carbon. Silicon dioxide and activated carbon, in particular silicon dioxide for nickel and activated carbon for palladium, are preferred.

The catalysts may optionally contain other metals as promoters. Promoters may be present, for instance, in amounts of 0 to 5 wt % with reference to palladium or nickel. Examples of promoters are zirconium, titanium, vanadium, niobium, tantalum, thallium, tin and/or copper.

Reaction of compounds of the formula (I) with hydrogen may be performed at atmospheric pressure or at an elevated pressure, up to 20 bar for example. The process is preferably performed at atmospheric pressure. The temperature for this reaction may be in the range 20° to 550° C. for example Temperatures between 120° and 480° C. in particular those of 250° to 450° C., are preferred.

The gas mixture present after this reaction can be worked up, for example, by condensing the organic components and then performing a hydrogenation reaction. It is preferable to separate out the 1,1,1,4,4,4,-hexafluorobutane already contained in the condensed organic material, by distillation for example, before subsequent hydrogenation.

Subsequent hydrogenation of the organic condensate, which preferably no longer contains 1,1,1,4,4,4-hexafluorobutane, can be performed in the same way as the previously described reaction of compounds of the formula (I) with hydrogen. In principle, the subsequent hydrogenation can also be performed in accordance with conventional hydrogenations from the prior art, i.e. any known hydrogenation catalysts can be used under the relevant known reaction conditions.

It is extremely surprising that it is possible to obtain 1,1,1,4,4,4-hexafluorobutane in good yield by using the process according to the invention because this product is not formed during the processes from the prior art which were described at the beginning.

EXAMPLES

Example 1

93.5 g/h of 1,1,1-trifluoro-2,2,2-trichloroethane and 22 Nl/h of hydrogen were passed, at a temperature of 400° C., over 200 ml of a catalyst which contained 5 g of palladium on 1 l of activated carbon. The gas stream was cooled to −78° C. after the catalyst and 48 g of crude product was obtained in this way over the course of 1 hour. According to analysis by gas chromatography, this product contained 17.6 wt.% of 1,1,1,4,4,4-hexafluorobutane. The more volatile components, which were lighter than 1,1,1,4,4,4-hexafluorobutane, were separated from the mixture and again passed over the catalyst under the previously mentioned conditions. 1,1,1,4,4,4-hexafluorobutane was obtained from this subsequent hydrogenation with a selectivity of 97%.

Example 2

38.5 g/h of 1,1,1-trifluoro-2,2,2-trichloroethane and 11 Nl/h of hydrogen were passed, at a temperature of 300° C., over 200 ml of a catalyst which contained 5 g of palladium on 1 l of activated carbon. The gas stream was cooled to −78° C. after the catalyst and 3.4 g of crude product was obtained in this way over the course of 1 hour. According to analysis by gas chromatography, this product contained 11 wt.% of 1,1,1,4,4,4-hexafluorobutane. The volatile components which were lighter than 1,1,1,4,4,4-hexafluorobutane were separated from this mixture and again passed over the catalyst under the previously mentioned conditions. 1,1,1,4,4,4-hexafluorobutane was obtained from this subsequent hydrogenation with a selectivity of 98%.

Example 3

99.2 g/h of 1,1,1-trifluoro-2,2,2-trichloroethane and 22 Nl/h of hydrogen were passed, at a temperature of 300° C., over 200 ml of a catalyst which contained 500 g of nickel doped with 0.5 wt.% of zirconium on 1 l of silicon dioxide. The gas stream was cooled to −78° C. after the catalyst and 74 g of crude product was obtained in this way over the course of 1 hour. According to analysis by gas chromatography, this product contained 7 wt.% of 1,1,1,4,4,4-hexafluorobutane. The volatile components which were lighter than 1,1,1,4,4,4-hexafluorobutane were separated from this mixture and again passed over the catalyst, under the previously mentioned conditions. 1,1,1,4,4,4-hexafluorobutane was obtained from this subsequent hydrogenation with a selectivity of 94%.

Example 4

The same procedure as described in example 3 was used, but only 94.4 g/h of 1,1,1-trifluoro-2,2,2-trichloroethane were used. 52 g of crude product was obtained which contained 38 wt.% of 1,1,1,4,4,4-hexafluorobutane. Subsequent hydrogenation yielded 1,1,1,4,4,4-hexafluorobutane with a selectivity of 93%.

Example 5

66 g/h of 1,1,1-trifluoro-2-bromoethane and 11 Nl/h of hydrogen were passed, at a temperature of 400° C., over 200 ml of a catalyst which contained 8 g of nickel on 1 l of activated carbon. The gas stream was cooled to −78° C. after the catalyst and 10 g of crude product was obtained in this way over the course of 1 hour. According to analysis by gas chromatography, this product contained 6 wt % of 1,1,1,4,4,4-hexafluorobutane The volatile components which were lighter than 1,1,1,4,4,4-hexafluorobutane were separated from this mixture and again passed over the catalyst., under the previously mentioned conditions. 1,1,1,4,4,4-hexafluorobutane was obtained from this subsequent hydrogenation with a selectivity of 98%.

We claim:

1. A process for preparing 1,1,1,4,4,4-hexafluorobutane, comprising reacting a trifluoroethane compound of the formula (I)

$$CF_3—CXYZ \qquad (I)$$

wherein X and Y independently of each other represent hydrogen, chlorine, or bromine and Z represents chlorine or bromine, with hydrogen in the gas phase and without a diluent on a palladium-containing supported catalyst and subsequently hydrogenating the reaction product, optionally after separating out 1,1,1,4,4,4-hexafluorobutane.

2. A process according to claim 1 wherein said trifluoroethane compound is selected from the group consisting of $CF_3—CCl_3$, $CF_3—CHCl_2$ and $CF_3—CH_2BR$.

3. A process according to claim 1, wherein the catalyst contains 0.5 to 20 g of palladium and/or 100 to 1000 g of nickel per litre.

4. A process according to claim 1, wherein the reaction is performed at temperatures in the range 20° to 550° C.

5. A process according to claim 1, wherein 1,1,1,4,4,4-hexafluorobutane is separated from the reaction product before subsequent hydrogenation.

6. A process according to claim 5, wherein the subsequent hydrogenation is performed in the same way as the reaction of the compound of formula (I) with hydrogen.

\* \* \* \* \*